United States Patent

Bruegger et al.

[11] Patent Number: 5,871,736
[45] Date of Patent: Feb. 16, 1999

[54] LIQUID IMMUNOGLOBULIN FORMULATIONS

[75] Inventors: René Bruegger, Berne; Katharina Gennari, Meikirch; Gerhard Hodler, Worb; Bernard Wuest, Villars-sur-Glâne, all of Switzerland

[73] Assignee: Red Cross Foundation Central Laboratory Blood Transfusion Service SRC, Berne, Switzerland

[21] Appl. No.: 813,219

[22] Filed: Mar. 7, 1997

Related U.S. Application Data

[63] Continuation-in-part of PCT/EP95/035,222 Sep. 7, 1995.

[30] Foreign Application Priority Data

Sep. 8, 1994 [GB] United Kingdom .................. 9418092

[51] Int. Cl.$^6$ .................................................. A61K 39/395
[52] U.S. Cl. ....................................... 424/177.1; 530/390.5
[58] Field of Search ........................ 424/177.1; 530/390.5

[56] References Cited

U.S. PATENT DOCUMENTS 4,360,457  11/1982  Ono et al. ............................. 530/390.5

FOREIGN PATENT DOCUMENTS

| 025275 | 3/1981 | European Pat. Off. . |
| 037078 | 10/1981 | European Pat. Off. . |
| 187712 | 7/1986 | European Pat. Off. . |
| 196761 | 10/1986 | European Pat. Off. . |
| 392717 | 10/1990 | European Pat. Off. . |

OTHER PUBLICATIONS

Derwent AN 85–193554 (1985).

Derwent AN 93–261569 (1993).

*Primary Examiner*—David Saunders
*Attorney, Agent, or Firm*—Hesna J. Pfeiffer; Diane E. Furman

[57] ABSTRACT

Immunoglobulin preparations, particularly liquid preparations of immunoglobulin G for intravenous infusion, are stabilized against dimer formation by the addition of one or more amphiphilic stabilizers. Preferred amphiphilic stabilizers are nicotinic acid derivatives, particularly nicotinamide, and naturally-occurring α-amino acids having a lipophilic side chain, for example phenylalanine, proline, leucine and isoleucine.

17 Claims, No Drawings

LIQUID IMMUNOGLOBULIN FORMULATIONS

This application is a continuation-in part of International application No. PCT/EP95/03522, filed Sep. 7, 1995, published as WO 96/07429, and designating the USA.

This invention relates to stable preparations of immunoglobulins.

A number of processes are known for the production of immunoglobulin preparations, particularly intravenously injectable forms of IgG (iv-IgG) from fractions of human blood plasma. In order for the product to be intravenously injectable, it is necessary to remove or to avoid the formation of aggregates which have anticomplementary activity and which, if injected intravenously, can give rise to severe side reactions including anaphylactic shock. The majority of iv-IgG preparations available for clinical use are lyophilized (freeze-dried) for improved stability on storage, but such preparations must be reconstituted with diluent, e.g. sterile water or saline, before use. This reconstitution step is inconvenient and time-consuming, and opens up the possibility of contamination of the product. It is therefore desirable to produce pharmaceutical compositions of iv-IgG which are intended to be stored and used in liquid (aqueous solution) form and which have the necessary degree of stability for such storage. Such compositions are referred to hereinafter as liquid preparations of iv-IgG. Some such preparations are already commercially available.

Although IgG products for intravenous injection contain only very small amounts of aggregates (trimers or higher polymers of IgG molecules), they may contain quite large amounts of IgG dimers, as may be determined for example by high pressure liquid chromatography (HPLC). These dimers do not give rise to anaphylactic shock, and generally have not been regarded as a problem. Indeed in many product specifications, monomers and dimers are considered together under a heading such as "functional IgG".

It has been found by Tankersley et al (Molecular Immunology 25, 41–48 1988) that the dimer content of IgG preparations is higher the more donors contribute to the plasma pool from which the IgG was obtained. Thus dimer cannot be detected in IgG obtained from a single individual and is relatively low in hyperimmune IgG obtained from a few hundred to a few thousand donors who have been immunised against a specific disease antigen, whereas it reaches high levels in IgG prepared from donor pools of 10,000 or more donors. The authors conclude that the IgG dimers are idiotype-anti-idiotype dimers which are formed when an antibody from one donor recognises the antigen-binding region of an antibody from a different donor and binds to it. Dimers and monomers are present in equilibrium, and the dimer content increases with total immunoglobulin concentration.

The same authors found that dimer formation increases with storage time; the dimer content of a typical preparation may double during the first week of storage, and continue to rise slowly thereafter. When an IgG preparation is lyophilized shortly after it is produced, this increase in dimer formation is prevented from taking place. However if the preparation is intended to be stored and used in liquid form, the dimer concentration will increase on storage.

The same type of dimer formation may occur in immunoglobulins other than IgG, for example in IgA, IgD and IgE. Furthermore, dimer formation is also observed in preparations of monoclonal antibodies, although the mechanism of dimer formation in MAbs may differ from that proposed by Tankersley et al.

It has now been found by the present inventors that although IgG dimer, unlike higher polymers, does not cause anaphylactic shock, nevertheless IgG preparations with a high dimer content are less well tolerated on intravenous injection and can give rise to undesirable side effects including fever, nausea and sometimes lowered blood pressure. Hypotensive side effects have been detected in a rat model by Bleeker et al (Vox Sanguinis 52, 281–290, 1987), and this also shows an apparent correlation with the dimer content. It is therefore desirable to stabilize preparations of immunoglobulins, particularly liquid preparations of iv-IgG, against dimer formation.

A number of additives have been used to stabilize iv-IgG and to improve tolerance to it on iv injection. These include glycine; disaccharides, e.g. maltose and saccharose; sugar alcohols, e.g. sorbitol; polyethylene glycol; or small quantities of surfactants such as PEG-20-sorbitanmonooleate or PEG-10-nonyloxyphenol. However, it is found that none of these conventional stabilizers are effective in inhibiting dimer formation in liquid preparations of iv-IgG.

Since dimer content is a function of Ig concentration, it is of course possible to reduce dimer content by dilution of the liquid IgG preparations. This approach is not practical, however, as it would require the infusion of unacceptably high volumes of liquid into the patients.

According to the present invention, the problem is solved by the addition to the immunoglobulin formulation of an effective amount of an amphiphilic stabilizer.

Amphiphilic stabilizers used according to the invention are substances which contain within the molecule a strongly or moderately hydrophilic region as well as a strongly or moderately lipophilic region, but which are not tensides, that is, they do not form micelles in aqueous solution at the concentrations at which they are used, but remain in monomeric form. The amphiphilic stabilizers of the invention contain within the molecule one or more groups selected from carboxylic acid, sulphonic acid, phosphoric acid, (all in free acid or pharmacologically acceptable salt form), keto-, aldehyde, hydroxy-, amino- and amide groups; as well as one or more lipophilic groups containing from 3 to 12 carbon atoms, preferably from 4 to 10 carbon atoms, and optionally one atom of nitrogen or sulphur. These groups are preferably selected from straight or branched chain alkyl groups, straight or branched chain alkenyl groups, and aromatic, heteroaromatic, aliphatic or heteroaliphatic rings. Ester groups may also be included as moderately hydrophilic groups.

If a nitrogen atom is present in the lipophilic group, it is preferably in tertiary form, for example in a pyridine ring. Preferred non-cyclic lipophilic groups are branched-chain alkyl groups containing from 4 to 10, preferably 4 to 6 carbon atoms.

Clearly any compound used as stabilizer for iv-IgG must itself be pharmaceutically acceptable for intravenous injection at the concentrations used. It is also preferred that it does not chemically change the IgG molecule, and that it has no significant buffer capacity at pH values between pH 4 and pH 8.

One group of preferred amphiphilic stabilizers are nicotinic acid and its derivatives, for example nicotinamide, nicotinamide N-oxide and N'-methyl nicotinamide, of which nicotinamide is particularly preferred.

A further preferred group of amphiphilic stabilizers, which may be used in conjunction with the first group, is that of naturally-occurring α-amino acids having uncharged lipophilic side-chains, as well as derivatives of such amino acids in which the carboxylic acid group is replaced by a group of formula —CONH$_2$, —CONHR, —CH$_2$OH, or —COOR, where R is C$_{1-4}$-alkyl. Such amino acids are phenylalanine, methionine, leucine, isoleucine, proline and valine, of which phenylalanine, proline, leucine and isoleucine; particularly proline, leucine and isoleucine; more particularly proline are preferred.

Japanese Patent Publication No 61-194035 discloses liquid gamma-globulin preparations which are subjected to heat treatment in the presence of a stabilizer which is a monosaccharide, disaccharide or sugar alcohol in the amount of 10–100 g/100 ml and an auxiliary stabilizer which may be a neutral amino acid for example valine, leucine or isoleucine, or a salt of a carboxylic acid.

The present invention provides a liquid immunoglobulin preparation, particularly a liquid preparation of immunoglobulin G for intravenous injection, containing one or more non-tenside amphiphilic stabilizers characterized in that they contain within the molecule one or more groups selected from carboxylic acid, sulphonic acid, keto-, aldehyde, hydroxy-, amino-, amide and ester groups; as well as one or more lipophilic groups containing from 3 to 12 carbon atoms and optionally one atom of nitrogen or sulphur, in a total amount of at least 0.2 mmol per gram of immunoglobulin and at a total concentration of at least 20 mmol/liter, at least one amphiphilic stabilizer being a compound of formula I, II or III below:

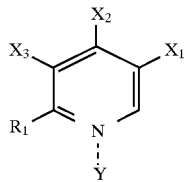   I in which the dashed line between N and Y indicates a bond where Y is —CH$_3$—O, or —(CH$_2$)$_n$—SO$_3$ where n is 1 or 2, N then having a positive charge; or the dashed line between N and Y indicates that the Y group can be absent;

R$_1$ is H, —OH, or methyl;

X$_1$, X$_2$ and X$_3$, independently, are H, —COZ, —SO$_3$H or —CH$_2$—Z$_1$, provided that at least one of X$_1$, X$_2$ and X$_3$ is H; but not all three are H;

Z is —OR or N(R)$_2$, where each R, independently, is H or C$_{1-3}$ alkyl;

Z$_1$ is a residue of a natural α-amino acid or an amide or ester therof, attached at the α-carbon atom;

   II in which

R$_3$ is —COZ, —SO$_3$H, —CH$_2$—CO—COOH, —CH(COOH)$_2$, or a group of formula —Q—Z$_1$ or —Q—Z$_2$, where Q is —CH$_2$— or —CO—;

Z and Z$_1$ are as defined above; and

Z$_2$ is a residue of a natural α-amino acid or an amide or ester therof, attached at the nitrogen atom of the α-amino group;

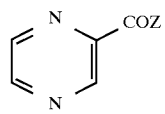   III in which Z is as defined above.

Preferably, in the compounds of formula I, two of the groups X$_1$, X$_2$, and X$_3$, more preferably X$_2$ and X$_3$, are hydrogen, and the third is —COZ. Preferably R$_1$ is H. The group Z$_1$ is preferably the residue of glycine, i.e. the group —CH(COOH)NH$_2$.

More preferably, the compound of formula I is nicotinic acid or a nicotinic acid derivative; that is, a compound of formula I in which X$_1$ is —COZ, and X$_2$ and X$_3$ are hydrogen. Nicotinamide, in which X$_1$ is —CONH$_2$, X$_2$ and X$_3$ are H, R$_1$ is H and Y is absent, is particularly preferred.

In the compounds of formula II, R$_3$ is preferably one of the groups —CONH$_2$, —CH$_2$—CO—COOH, or —CH(COOH)$_2$; or a group of formula —Q—Z$_2$. Examples of groups Z$_2$ are those derived from glycine ethyl ester and L-arginine, i.e. groups of formula:

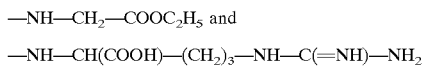

The preferred compound of formula II is benzamide.

Preferred stabilizers are compositions comprising nicotinamide together with one or more of the above amphiphilic amino acids or their derivatives. More preferred stabilizer compositions comprise nicotinamide and proline, optionally together with one or more additional amphiphilic amino acids. Especially preferred compositions are mixtures of (a) nicotinamide and proline; (b) nicotinamide, proline and isoleucine; and (c) nicotinamide, proline, isoleucine and leucine. Preferably in such compositions the mole ratio of nicotinamide to total amphiphilic amino acids lies between 1:1 and 1:4. The most preferred composition is a mixture of nicotinamide, proline and isoleucine, preferably in a mole ratio of 1:(0.8–2.0):(0.8–2.0).

The immunoglobulin stabilized according to the invention may be any preparation of IgA, IgD, IgE or IgG, whether polyclonal or monoclonal, and whether isolated from human or animal blood plasma or produced by other means, for example by hybridoma or recombinant DNA technology. Preferably it is a preparation of IgG from human blood plasma which has been treated so as to be intravenously injectable and which is intended to be stored and used in liquid form. More preferably it is a polyvalent, intact immunoglobulin which has not been cleaved (for example with high pepsin concentrations) and which retains the structural and functional integrity of the 7S-IgG antibodies, including an intact Fc region. Preferably it is one obtained from blood serum fractions by a modified alcohol cryoprecipitation including treatment with low concentrations of pepsin at pH 4.

The IgG content of the liquid formulation is preferably between 3% and 16%, more preferably between 6% and 12%. The pH of the solution is preferably from pH 4 to pH 8, more preferably from pH 5 to pH 6, particularly from pH 5.2 to pH 5.4. At such relatively acidic pH values, it is important that the solution have low buffer capacity, to prevent any significant lowering of the pH of the recipient's blood upon intravenous injection. The tonicity of the solution may be adjusted to physiological values by the addition of one or more non-buffering substances for example sodium chloride, glycine, sucrose, maltose and sorbitol.

Such liquid formulations may be administered by intravenous infusion for example at a dosage of 0.2–1.0 g of IgG per kg of body weight per day.

The quantity of amphiphilic stabilizer present in the compositions according to the invention is preferably from 0.2 to 6 mmol per gram of IgG, more preferably 1 to 3 mmol/g IgG. The immunoglobulin preparations may also contain other proteins, for example albumin.

A liquid iv-IgG preparation according to the invention containing an amphiphilic stabilizer may be stored for up to 2 years at temperatures between 2° C. and 25° C. without the dimer content rising to unacceptable levels. Such formulations are well tolerated upon intravenous injection.

Solutions of iv-IgG which are intended to be lyophilized and sold in solid lyophilized form may also be stabilized by adding amphiphilic stabilizers according to the invention, so as to reduce dimer formation during the time between preparation and lyophilization.

The following examples illustrate the invention:

A. Preparative procedure for liquid iv-IgG preparation

Crude IgG paste obtained by alcohol fractionation of pooled human blood plasma is dissolved in sterile water at 4° C. and filtered. The solution is acidified to pH 4 and incubated with a small quantity of pepsin at pH 4, 37° C., then neutralized. The product is then diafiltered to remove any remaining alcohol, then the pH is adjusted to pH 5.3 and the solution is concentrated by ultrafiltration to give a final protein concentration of between 6% and 15% w/v.

The product may also be prepared as described in Swiss Patent No. 684 164.

B. Measurement of Dimer Content

The product is analysed by HPLC on a Hewlett Packard HP 1090, using a TSK G3000SW-XL column of dimensions 7.8×300 mm with a mobile phase of 0.04M phosphate buffer and 0.2M sodium chloride at pH 7.0. The flow rate is 0.7 ml/min. A sample of 1.3 μl of a 150 mg/ml solution is used, and protein is detected by UV absorption at 280 nm. Peak areas corresponding to aggregate (typical retention time 8–9 min), dimer (9–10.5 min) and monomer (10.5–13.5 min) are measured automatically, and dimer content is given by $$D\% = \frac{AD}{AA + AD + AM} \times 100$$

where AA, AD and AM are the areas of the aggregate, dimer and monomer peaks respectively.

C. Stability Tests

Liquid iv-IgG preparations are stored at ambient temperature (20°–25° C.) in sealed containers for periods of up to five months, and the dimer content measured at the end of this period.

EXAMPLE 1

To 1 liter of the standard liquid preparation prepared as in A above and having a protein content of 15% and a pH of 5.3 is added 24.75 g phenylalanine (150 mmol/L, 1 mmol/g protein).

Stability data for Example 1 and for additional Examples 2–41 according to the invention, together with comparative examples A–H containing no additives or containing glycine only, are shown in Tables 1–4 below. Table 5 below shows the results of testing four liquid preparations each containing 12% protein in the rat hypotensive model as described by Bleeker et al (Vox Sanguinis 52, 281–290, 1987) after room temperature storage. Preparations according to the invention (Examples 42–44) gave only a 5%–18% drop in blood pressure whereas the unstabilized preparation I gave a drop of nearly 50%.

TABLE 1

Dimer content after 80 days storage

| Example | Additives | Concentration of additive (mmol/L) | Concentration of protein (% w/v) | Dimer Content |
|---|---|---|---|---|
| A | None | — | 15 | 20.2% |
| 1 | Phenylalanine | 150 | 15 | 14.7% |
| 2 | Phenylalaninamide | 150 | 15 | 12.5% |
| 3 | Phenylalaninol (2-amino-3-phenyl-1-propanol) | 150 | 15 | 13.1% |
| 4 | 2-phenylethylamine | 150 | 15 | 11.7% |
| B | None | — | 12 | 17.7% |
| 5 | Nicotinamide | 120 | 12 | 12.5% |
| 6 | Nicotinic acid | 120 | 12 | 13.3% |
| 7 | Nicotinamide + Phenylananine | 120 120 | 12 | 10.3% |

TABLE 2

Dimer content after 90 days storage

| Example | Additives | Concentration of additive (mmol/L) | Concentration of protein (% w/v) | Dimer Content |
|---|---|---|---|---|
| C | none | — | 15 | 18.0% |
| D | Glycine | 300 | 15 | 17.4% |
| 8 | Glycine Phenylalanine | 200 140 | 15 | 12.6% |
| 9 | Glycine Nicotinamide | 200 150 | 15 | 10.7% |
| E | none | — | 6 | 11.4% |
| F | Glycine | 300 | 6 | 11.2% |
| 10 | Glycine Phenylalanine | 300 60 | 6 | 9.3% |
| 11 | Glycine Nicotinamide | 300 60 | 6 | 8.7% |
| 12 | Methionine Leucine | 60 60 | 6 | 9.8% |
| G | none | — | 12 | 17.5% |
| 13 | Proline Nicotinamide | 200 100 | 12 | 10.6% |
| 14 | Proline Leucine Isoleucine Nicotinamide | 100 60 60 100 | 12 | 10.0% |
| 15 | Proline Leucine Isoleucine Nicotinamide | 120 80 80 80 | 12 | 10.1% |
| 16 | Proline Isoleucine Nicotinamide Glycine | 100 120 100 40 | 12 | (70 days only) 9.4% |

TABLE 3

Dimer content after 1 month and 5 months storage
In all cases, the additive is present at 80 mmol/L, and the protein content is 12%

| Example | Additive | Dimer content after 1 month | dimer content after 5 months |
|---|---|---|---|
| G | None | 16.9% | 19.3% |
| 17 | isonicotinic acid amide | 11.7% | 13.5% |
| 18 | isonicotinic acid | 15.2% | 17.5% |
| 19 | pyridine 3,5-dicarboxylic acid | 14.0% | 16.3% |

TABLE 3-continued

Dimer content after 1 month and 5 months storage
In all cases, the additive is present at 80 mmol/L, and
the protein content is 12%

| Example | Additive | Dimer content after 1 month | dimer content after 5 months |
|---|---|---|---|
| 20 | 6-methylnicotinic acid | 12.4% | 14.3% |
| 21 | benzamide | 11.8% | 13.7% |
| 22 | nicotinamide | 11.2% | 14.2% |
| 23 | nicotinamide N-oxide | 12.1% | 14.9% |
| 24 | N-methylnicotinamide | 11.9% | 13.8% |
| 25 | 1-methylnicotinamide | 13.2% | 15.3% |
| 26 | nicotinic acid | 14.4% | 16.7% |
| 27 | nicotinic acid N-oxide | 14.4% | 17.0% |
| 28 | methyl nicotinate | 10.7% | 12.1% |

TABLE 4

Dimer content after 1 month storage
In all cases, the additive is present at 50 mmol/L, and
the protein content is 12%

| Example | Additive | Dimer content |
|---|---|---|
| H | none | 19.1% |
| 29 | nicotinamide | 15.5% |
| 30 | 6-hydroxynicotinic acid | 17.7% |
| 31 | 3-(3-pyndyl)-D-alanine | 17.0% |
| 32 | pyridine-3-sulfonic acid | 17.0% |
| 33 | 3-(1-pyridino)-1-propane-sulfonic acid | 16.6% |
| 34 | benzamide | 15.5% |
| 35 | benzylmalonic acid | 16.0% |
| 36 | phenylpyruvic acid | 15.5% |
| 37 | N-benylglycine ethyl ester | 15.9% |
| 38 | N-benzoyl-L-arginine | 15.3% |
| 39 | benzene sulfonic acid | 17.1% |
| 40 | pyrazine carboxylic acid | 16.6% |
| 41 | pyrazineamide | 15.8% |

TABLE 5

Dimer content and blood pressure drop in rat model
Protein concentration 12%

| Example | Additives | Conc. (mmol/L) | Dimer content | Blood pressure drop |
|---|---|---|---|---|
| I | None | — | 16.0% | 49% |
| 42 | Glycine | 100 | 7.8% | |
| | Phenylalanine | 120 | | |
| | Nicotinamide | 120 | | |
| 43 | Proline | 200 | 8.4% | 18% |
| | Nicotinamide | 100 | | |
| 44 | Proline | 100 | 7.9% | 6% |
| | Leucine | 60 | | |
| | Isoleucine | 60 | | |
| | Nicotinamide | 100 | | |

We claim:

1. A liquid immunoglobulin preparation containing one or more non-tenside amphiphilic stabilizers characterized in that they contain within the molecule one or more groups selected from carboxylic acid, sulphonic acid, keto-, aldehyde, hydroxy-, amino-, amide and ester groups; as well as one or more lipophilic groups containing from 3 to 12 carbon atoms and one or none atom of nitrogen or sulphur, in a total amount of at least 0.2 mmol per gram of immunoglobulin and at a total concentration of at least 20 mmol/liter, at least one amphiphilic stabilizer being a compound of formula I, II or III:

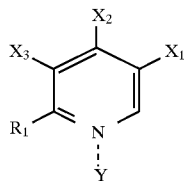
I in which
the dashed line between N and Y indicates a bond where Y is —$CH_3$—O, or —$(CH_2)_n$—$SO_3$ where n is 1 or 2, N then having a positive charge; or
the dashed line between N and Y indicates that the Y group can be absent;
$R_1$ is H, —OH, or methyl;
$X_1$, $X_2$ and $X_3$, independently, are H, —COZ, —$SO_3$H or —$CH_2$—$Z_1$, provided that at least one of $X_1$, $X_2$ and $X_3$ is H; but not all three are H;
Z is —OR or $N(R)_2$, where each R, independently, is H or $C_{1-3}$ alkyl;
$Z_1$ is a residue of a natural α-amino acid or an amide or ester thereof, attached at the α-carbon atom;

II in which
$R_3$ is —COZ, —$SO_3$H, —$CH_2$—CO—COOH, —CH$(COOH)_2$, or a group of formula —Q—$Z_1$ or —Q—$Z_2$, where Q is —$CH_2$— or —CO—;
Z and $Z_1$ are as defined above; and
$Z_2$ is a residue of a natural α-amino acid or an amide or ester thereof, attached at the nitrogen atom of the α-amino group:

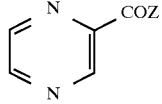
III in which Z is as defined above.

2. The preparation according to claim 1 which is a liquid preparation of immunoglobulin G for intravenous injection.

3. The preparation according to claim 1 containing a compound of Formula I in which two of the groups $X_1$, $X_2$ and $X_3$ are hydrogen, and the third is —COZ.

4. The preparation according to claim 3 in which the compound of formula I is nicotinic acid or a nicotinic acid derivative in which $X_1$ is COZ and $X_2$ and $X_3$ are H.

5. The preparation according to claim 4 in which the nicotinic acid derivative is nicotinamide.

6. The preparation according to claim 1 containing a compound of Formula II in which $R_3$ is one of the groups —COZ, —$CH_2$—CO—COOH, —CH$(COOH)_2$ or Q—$Z_2$.

7. The preparation according to claim 6 in which the compound of formula II is benzamide.

8. The preparation according to claim 1 in which the amphiphilic stabilizer, in addition to compounds I, II or III is an amino acid selected from the group consisting of phenylalanine, methionine, leucine, isoleucine, proline, valine, and a derivative of any of these in which the carboxylic acid group is replaced by a group of formula —$CONH_2$, —CONHR, —$CH_2OH$, or —COOR, where R is $C_{1-4}$ alkyl.

9. The preparation according to claim 8 in which at least one amphiphilic stabilizer is selected from proline, leucine and isoleucine.

10. The preparation according to claim 9 containing proline and nicotinamide.

11. The preparation according to claim 10 in which the mole ratio of nicotinamide to total amino acid is between 1:1 and 1:4.

12. The preparation according to claim 11 containing nicotinamide, proline and isoleucine as the only amphiphilic stabilizers.

13. The preparation according to claim 12 in which the said stabilizers are present in a mole ratio of 1:(0.8–2.0):(0.8–2.0).

14. The liquid preparation according to claim 1 having a pH between pH 5 and pH 6.

15. A method for the stabilization of liquid preparations of iv-IgG against dimer formation upon storage at a temperature between 2° C. and 25° C. comprising the step of adding to the preparation at least 20 mmol/liter of one or more non-tenside amphiphilic stabilizers characterized in that they contain within the molecule one or more groups selected from carboxylic acid, sulphonic acid, keto-, aldehyde, hydroxy-, amino-, amide and ester groups; as well as one or more lipophilic groups containing from 3 to 12 carbon atoms and one or no atom of nitrogen or sulphur, in a total amount of at least 0.2 mmol per gram of immunoglobulin, at least one amphiphilic stabilizer being a compound of formula I, II or III:

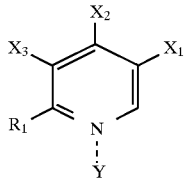

in which
the dashed line between N and Y indicates a bond where Y is —$CH_3$—O, or —$(CH_2)_n$—$SO_3$ where n is 1 or 2, N then having a positive charge; or
the dashed line between N and Y indicates that the Y group can be absent; and $R_1$ is H, —OH, or methyl;

$X_1$, $X_2$ and $X_3$, independently, are H, —COZ, —$SO_3$H or —$CH_2$—$Z_1$, provided that at least one of $X_1$, $X_2$ and $X_3$ is H; but not all three are H;

Z is —OR or $N(R)_2$, where each R, independently, is H or $C_{1-3}$ alkyl;

$Z_1$ is a residue of a natural α-amino acid or an amide or ester thereof, attached at the α-carbon atom;

in which $R_3$ is —COZ, —$SO_3$H, —$CH_2$—CO—COOH, —CH$(COOH)_2$, or a group of formula —Q—$Z_1$ or —Q—$Z_2$, where Q is —$CH_2$— or —CO—;

Z and $Z_1$ are as defined above; and $Z_2$ is a residue of a natural α-amino acid or an amide or ester thereof, attached at the nitrogen atom of the α-amino group:

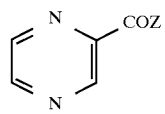

in which Z is as defined above.

16. The method according to claim 15 in which the preparation is not subjected to any heat treatment step involving temperatures above 50° C.

17. The method for the preparation of a lyophilized preparation of iv-IgG having a low dimer content, comprising the step of lyophilization of a liquid preparation stabilized by the method of claim 15.

* * * * *